US011000530B2

(12) United States Patent
El-Shabrawi

(10) Patent No.: US 11,000,530 B2
(45) Date of Patent: May 11, 2021

(54) METHODS AND COMPOSITIONS FOR THE TREATMENT OF OPHTHALMIC CONDITIONS

(71) Applicant: Murray & Poole Enterprises, Limited

(72) Inventor: Yosuf El-Shabrawi, Klagenfurt (AT)

(73) Assignee: MURRAY AND POOLE ENTERPRISES LTD, Gibraltar (GI)

( * ) Notice: Subject to any disclaimer, the term of this patent is extended or adjusted under 35 U.S.C. 154(b) by 0 days.

(21) Appl. No.: 16/118,484

(22) Filed: Aug. 31, 2018

(65) Prior Publication Data
US 2019/0070198 A1 Mar. 7, 2019

Related U.S. Application Data

(60) Provisional application No. 62/553,584, filed on Sep. 1, 2017.

(51) Int. Cl.
A61K 31/196 (2006.01)
A61K 31/573 (2006.01)
A61K 45/06 (2006.01)
A61P 27/02 (2006.01)
A61K 9/00 (2006.01)
A61K 9/06 (2006.01)
A61K 31/5383 (2006.01)
A61K 47/32 (2006.01)
A61K 47/40 (2006.01)
A61K 31/58 (2006.01)

(52) U.S. Cl.
CPC .......... A61K 31/573 (2013.01); A61K 9/0048 (2013.01); A61K 9/06 (2013.01); A61K 31/196 (2013.01); A61K 31/5383 (2013.01); A61K 45/06 (2013.01); A61K 47/32 (2013.01); A61K 47/40 (2013.01); A61P 27/02 (2018.01); A61K 31/58 (2013.01)

(58) Field of Classification Search
CPC ..... A61K 31/573; A61K 31/196; A61K 45/06

USPC .......................................................... 514/170
See application file for complete search history.

(56) References Cited

U.S. PATENT DOCUMENTS

2006/0183698 A1* 8/2006 Abelson ................. A61K 45/06
                                                           514/35
2015/0164882 A1   6/2015 Dilzer et al.
2016/0243031 A1   8/2016 Wiley et al.
2017/0209500 A1*  7/2017 Moloney ................ A61K 35/63

FOREIGN PATENT DOCUMENTS

WO    2007012974 A2    2/2007

OTHER PUBLICATIONS

Loftsson and Stefansson, Acta Ophthalmol (2002), vol. 80, pp. 144-150. (Year: 2002).*
International Search Report and Written Opinion dated Nov. 20, 2018, International Application No. PCT/EP2018/073494, pp. 1-12.

* cited by examiner

Primary Examiner — Jared Barsky
Assistant Examiner — Janet L. Coppins
(74) Attorney, Agent, or Firm — Biopharma Law Group, PLLC

(57) ABSTRACT

Compositions comprising at least two of a corticosteroid, a non-steroidal anti-inflammatory drug (NSAID), and an antibiotic find use in treating or preventing eye conditions in subjects in need thereof. Methods of treatment or prevention of eye conditions comprise administering an effective amount of the disclosed compositions to the affected eye(s). Methods of preparing a composition comprising an NSAID, a corticosteroid, and an antibiotic comprise separately complexing the NSAID and antibiotic with cyclodextrin.

13 Claims, No Drawings

METHODS AND COMPOSITIONS FOR THE TREATMENT OF OPHTHALMIC CONDITIONS

PRIORITY

This application claims priority to, and the benefit of, U.S. Provisional Patent Application Ser. No. 62/553,584, filed Sep. 1, 2017, which is hereby incorporated by reference in its entirety.

BACKGROUND

Inflammatory reactions can cause tissue damage, promoting scar formation. In the eye and its appendages, this condition can lead to undesired functional impairments. For this reason, after cataract and other eye surgeries, medications such as anti-inflammatory drugs are often administered to aid in the healing process. The anti-inflammatory drugs are typically delivered to the ocular surface and the front of the eye in the form of eye drops.

The separate application of two or more different active ingredients is not ideal for both compliance and pharmacokinetic reasons. Many patients undergoing ocular surgery, particularly cataract surgery, are of an advanced age with impaired vision, making it difficult to handle the administration of multiple formulations. Further, contact time and absorption of the applied active ingredients are difficult to calculate due to their reciprocal displacement from the tear film. In order to avoid mistakes when administering multiple preparations, the patient must strictly adhere to application intervals. In contrast, if a combination product is used, i.e., a product comprising at least two active agents, each of the active ingredients are applied to the conjunctival sac in a defined proportion, so that reciprocal displacement can be ruled out.

Therefore, there is a need in the art for a combination product that comprises at least two therapeutically active agents useful for treating or preventing ophthalmic conditions and is characterized by improved compliance, improved efficacy, and reduction of side effects associated with topical administration of medications.

BRIEF SUMMARY

Disclosed herein are ophthalmic compositions comprising at least two of the following therapeutically active agents: a corticosteroid, a non-steroidal anti-inflammatory drug (NSAID), and an antibiotic. Such compositions find use in treating or preventing ophthalmic conditions, such as ocular inflammation or ocular infection that can occur after eye surgery. In one embodiment, the ophthalmic composition is in the form of liquid drops, a gel, or an ointment, and a therapeutically effective amount of the ophthalmic composition is applied topically to at least one affected eye of a subject having an ophthalmic condition or at risk for developing an ophthalmic condition in order to treat or prevent the condition.

According to aspects of the invention illustrated herein, there is provided a composition comprising a non-steroidal anti-inflammatory drug (NSAID) and a corticosteroid. In accordance with aspects of the present invention, the composition may further include an antibiotic. In accordance with yet further aspects of the present invention, the composition may further include a complexing agent. In accordance with yet further aspects of the present invention, the composition may further include a viscosifying agent.

According to aspects of the invention illustrated herein, there is provided a composition comprising a corticosteroid, a non-steroidal anti-inflammatory drug (NSAID), an antibiotic, and optionally a viscosifying agent, wherein the composition is formulated as an eye gel.

According to aspects of the invention illustrated herein, there is provided a method of treating and/or preventing an ophthalmic condition in a subject, the method comprising topically administering an effective amount of the composition to an eye of a subject in need thereof.

According to aspects of the invention illustrated herein, there is provided a method for preparing a composition comprising prednisolone, diclofenac, and ofloxacin in a gel formulation, the method can include: producing a methylcellulose gel to form Solution 1; complexing ofloxacin with gamma-cyclodextrin to form Solution 2; complexing diclofenac with gamma-cyclodextrin to form Solution 3; combining Solutions 2 and 3 to form Solution 4; adding mannitol to Solution 4 to form Solution 5; Solutions 1 and 5 to form Solution 6; and adding prednisolone acetate to Solution 6, thereby forming the composition, wherein steps a)-c) can be performed in any order, and wherein step a) can be performed before, simultaneously, or after any one of steps b)-f).

Methods for preparing the ophthalmic compositions are also provided herein and comprise separately complexing the NSAID and the antibiotic with cyclodextrin.

DETAILED DESCRIPTION

The present invention now will be described more fully hereinafter with reference to the accompanying experiments and/or drawings, in which some, but not all embodiments of the inventions are shown. It is to be understood that the following detailed description is provided to give the reader a fuller understanding of certain embodiments, features, and details of aspects of the invention, and should not be interpreted as a limitation of the scope of the invention. Indeed, many different embodiments are described below and the description provided below should not be construed as limited to only these embodiments; rather, these embodiments are provided so that this disclosure will satisfy applicable legal requirements. Like numbers refer to like elements throughout.

I. Definitions

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls Unless otherwise specified, all percentages and amounts expressed herein and elsewhere in the specification should be understood to refer to percentages by weight. The amounts given are based on the active weight of the material.

As used herein, the term "about" or "approximately" refers to a variation of 10% from the indicated values (e.g., 1.0%, 1.5%, 2.0%, etc.), or in case of a range of values, means a 10% variation from both the lower and upper limits of such ranges unless otherwise stated or otherwise evident from the context (except where such a number would exceed a possible value).

The term "eye condition" or "ophthalmic condition" refers to any of a wide variety of pathological ocular conditions or physiologic abnormalities of the eye, such as glaucoma, ocular inflammatory conditions such as keratitis, uveitis, allergy, and dry eye syndrome, ocular infections, ocular allergies, cancerous growth, neo vessel growth originating from the cornea, retinal edema, macular edema, diabetic retinopathy, retinopathy of prematurity, degenerative diseases of the retina (macular degeneration, retinal dystrophies), retinal diseases associated with glial proliferation, and the like. Non-limiting ophthalmic conditions that are treated with the presently disclosed compositions and methods include, but are not limited to, age related macular degeneration, alkaline erosive keratoconjunctivitis, allergic conjunctivitis, allergic keratitis, anterior uveitis, Behcet's disease, blepharitis, blood-aqueous barrier disruption, chorioiditis, chronic uveitis, conjunctivitis, contact lens-induced keratoconjunctivitis, corneal abrasion, corneal trauma, corneal ulcer, crystalline retinopathy, cystoid macular edema, dacryocystitis, diabetic keratopathy, diabetic macular edema, diabetic retinopathy, dry eye disease, dry age-related macular degeneration, eosinophilic granuloma, episcleritis, exudative macular edema, giant cell arteritis, giant papillary conjunctivitis, glaucoma, glaucoma surgery failure, graft rejection, herpes zoster, inflammation after cataract surgery, iridocorneal endothelial syndrome, iritis, keratoconjunctiva sicca, keratoconjunctival inflammatory disease, keratoconus, necrotic keratitis, neovascular diseases involving the retina, uveal tract or cornea such as neovascular glaucoma, corneal neovascularization, neovascularization following a combined vitrectomy and lensectomy, neovascularization of the optic nerve, and neovascularization due to penetration of the eye or contusive ocular injury, neuroparalytic keratitis, non-infectious uveitisocular herpes, ocular lymphoma, ocular rosacea, ophthalmic infections, ophthalmic pemphigoid, optic neuritis, panuveitis, papillitis, pars planitis, persistent macular edema, phacoanaphylaxis, posterior uveitis, postoperative inflammation, proliferative diabetic retinopathy, proliferative sickle cell retinopathy, proliferative vitreoretinopathy, retinal artery occlusion, retinal detachment, retinal vein occlusion, retinitis pigmentosa, retinopathy of prematurity, rubeosis iritis, scleritis, Stevens-Johnson syndrome, sympathetic ophthalmia, temporal arteritis, thyroid associated ophthalmopathy, uveitis, vernal conjunctivitis, vitamin A insufficiency-induced keratomalacia, vitreitis, and wet age-related macular degeneration.

"Efficacy" means the ability of an active agent administered to a patient or subject to produce a therapeutic effect in the patient.

"Side effect" is defined herein as a secondary and usually adverse effect of a drug.

Terms such as "treating" or "treatment" or "to treat" or "alleviating" or "to alleviate" refer to therapeutic measures that cure, slow down, lessen symptoms of, reverse, and/or halt progression of a diagnosed pathologic condition or disorder. Thus, those in need of treatment include those already with the disorder. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein "preventing" refers to the administration of a therapeutically effective amount of the compositions described herein to a subject to protect the subject from developing inflammation and/or a pathological condition or disorder of the eye. Thus, the term "preventing" when used in the context of a disease or disease condition means prophylactic administration of the described compositions to stop or otherwise delay the onset of a pathological hallmark or symptom of the ocular disease or disorder.

A "pharmaceutical composition" is defined herein as comprising at least one therapeutic agent, otherwise known as active pharmaceutical agent (API), e.g., corticosteroid, NSAID, antibiotic, and at least one pharmaceutically acceptable carrier.

An "ophthalmic composition" or "ophthalmic preparation" or "ophthalmic formulation" or the like is defined herein as a pharmaceutical composition formulated for ocular administration.

"Pharmaceutically acceptable" means that which is generally safe, non-toxic and neither biologically nor otherwise undesirable and includes that which is acceptable for veterinary use as well as human pharmaceutical use.

The term "pharmaceutically acceptable carrier" refers to a carrier medium which does not interfere with the effectiveness of the biological activity of the active ingredient(s) and which is not excessively toxic to the host at a concentration at which it is administered. The term includes solvents, dispersion media, antibacterial and antifungal agents, isotonic agents, adsorption delaying agents, and the like. The use of such media and agents for pharmaceutically active substances is well known in the art (see, for example, "*Remington's Pharmaceutical Sciences*", E. W. Martin, 18$^{th}$Ed., 1990, Mack Publishing Co.: Easton, Pa., which is incorporated herein by reference in its entirety).

The terms "therapeutic agent", "drug", "pharmaceutically active substance", "active pharmaceutical ingredient" are used herein interchangeably. They refer to a substance, molecule, compound, agent, factor or composition effective in the treatment or prevention of a disease or condition.

As used herein, the term "effective amount", refers to any amount of a compound, agent or composition that is sufficient to fulfill its intended purpose(s), e.g., a desired biological or medicinal response in a tissue, system or subject. For example, in certain embodiments of the present invention, the purpose(s) may be: to slow down or stop the progression, aggravation, or deterioration of the symptoms of an eye condition, to bring about amelioration of the symptoms of the condition, and/or to cure the condition. Determination of an effective amount is well within the ordinary skill in the art of pharmaceutical sciences and medicine, in that it may depend on various biological factors or individual variations and response to treatments.

By "therapeutically effective dose or amount" is intended an amount of the ophthalmic composition that when administered brings about a positive therapeutic response with respect to treatment of a patient with an ophthalmic condition, e.g., an improvement in the condition can be evidenced by, for example, a delayed onset of clinical symptoms of the condition, a reduction in severity of some or all clinical symptoms of the condition, a slower progression of the condition, an improvement in the overall health or well-being of the subject, or by other parameters well known in the art that are specific to the particular condition.

By "prophylactically effective dose or amount" or is intended an amount of the ophthalmic composition that when administered to a patient at risk of developing an ophthalmic condition is able to prevent or slow the development of the condition.

The term "corticosteroid", as used herein, refers to any of a wide variety of drugs that are analogues of cortisol, a hormone which is naturally produced in the adrenal cortex, and function as an anti-inflammatory. Examples of corticosteroids include, but are not limited to, betamethasone, budenoside, cortisone, dexamethasone, hydrocortisone, methylprednisoline, prednisolone, prednisone, and triamcinolone. In certain preferred embodiments of the present invention, corticosteroids are effective in the treatment or prevention of an eye disease or condition via topical administration.

The term "non-steroidal anti-inflammatory drug" or "NSAID," as used herein, refers to a class of therapeutic agents with anti-inflammatory actions that are distinguished from the cyclic organic steroid compounds characterized by a four-ring steroidal structure. Examples of NSAIDs include, but are not limited to, diclofenac, ketorolac tromethamine, bromfenac, nepafenac, derivatives thereof, and salts thereof.

The terms "antibiotic," and "antibacterial" used interchangeably herein, refer to compounds that either kill (bactericidal) or inhibit the growth (bacteriostatic) of at least one species of bacteria.

The term "viscosifying agent" or "viscosifier," as used herein, refers to compounds that increase the viscosity of a liquid when added thereto.

As used herein, the term "physiologically tolerable salt" refers to any acid addition or base addition salt that retains the biological activity and properties of the corresponding free base or free acid, respectively, and that is not biologically or otherwise undesirable. Acid addition salts are formed with inorganic acids (e.g., hydrochloric, hydrobromic, sulfuric, nitric, phosphoric acids, and the like); and organic acids (e.g., acetic, propionic, pyruvic, maleic, malonic, succinic, fumaric, tartaric, citric, benzoic, mandelic, methanesulfonic, ethanesulfonic, p-toluenesulfonic, salicylic acids, and the like. Base addition salts can be formed with inorganic bases (e.g., sodium, potassium, lithium, ammonium, calcium, magnesium, zinc, aluminium salts, and the like), and organic bases (e.g., salts of primary, secondary and tertiary amines, substituted amines including naturally occurring substituted amines, cyclic amines, and basic ion exchange resins, such as isopropylamine, trimethylamine, diethylamine, triethylamine, tripropylamine, ethanolamine, 2-dimethyl-aminoethanol, 2-diethylaminoethanol, trimethamine, dicyclohexyl-amine, lysine, arginine, histidine, caffeine, procaine, hydrabanine, choline, betaine, ethylenediamine, glycosamine, methylglucamine, theobromine, purines, piperazine, N-ethylpiperidine, polyamine resins, and the like).

As used herein, the term "derivative" in the context of a chemical compound refers to a chemical analogue that resembles the chemical compound in structure and substantially retains the activity of the chemical compound.

The term "topical formulation" and "topical composition" are used herein interchangeably. They refer to a composition formulated such that the active ingredient(s) of the composition may be applied for direct administration to the surface of the eye and from which an effective amount of the active ingredient(s) is released. Examples of topical formulations include, but are not limited to, lotions, sprays, ointments, creams, gels, pastes, and the like.

The term "topical", when used herein to characterize the delivery, administration or application of a composition of the present invention, is meant to specify that the composition is delivered, administered or applied directly to the site of interest (i.e., to the eye) for a localized effect. Preferably, topical administration is effected without any significant absorption of components of the composition into the subject's blood stream (to avoid a systemic effect). In certain preferred embodiments of the present invention, topical administration of a composition is effected without any significant absorption of components of the composition into the subject's eye tissues, such as the aqueous humor, and corneal and conjunctival tissues.

The term "non-invasive", when used herein refers to a method or mode of administration that does not rupture or puncture (e.g., by a mechanical means) a biological membrane to which a therapeutic agent is being delivered.

The term "ophthalmic", as used herein in connection with a composition, refers to a composition intended to be administered to the eye and which presents a pharmaceutical effect.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, bears, and so on. The meaning of the terms "eukaryote", "animal", "mammal", etc. is well known in the art and can, for example, be deduced from Wehner and Gehring (1995; Thieme Verlag). In the context of this invention, it is also envisaged that animals are to be treated which are economically, agronomically or scientifically important. Scientifically important organisms include, but are not limited to, mice, rats, and rabbits. Non-limiting examples of agronomically important animals are sheep, cattle and pigs, while, for example, cats and dogs may be considered as economically important animals. In one embodiment, the subject/patient is a mammal; in another embodiment, the subject/patient is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orang-utan, a gibbon, a sheep, cattle, or a pig); in a further embodiment the subject/patient is a human. In many embodiments, the subject is a human being. The terms "individual" and "subject" do not denote a particular age, and thus encompass adults, children, and newborns.

II. Ophthalmic Compositions

Disclosed herein are ophthalmic compositions for administration to the eye for the treatment or prevention of eye conditions. The presently disclosed ophthalmic compositions eliminate the undesirable side effects that are generally associated with therapeutic ocular compositions.

The presently disclosed compositions comprise at least two of a corticosteroid, a non-steroidal anti-inflammatory drug (NSAID), and an antibiotic.

In one embodiment, the composition includes a corticosteroid, a non-steroidal anti-inflammatory medication (NSAID), and an antibiotic.

In other embodiments, the composition comprises a corticosteroid and an antibiotic.

In yet other embodiments, the composition comprises a corticosteroid and an NSAID.

In still other embodiments, the composition comprises an NSAID and an antibiotic.

Corticosteroids are the most frequently prescribed class of therapeutics in ophthalmology. In particular, topical corticosteroids have revolutionized the practice of ophthalmology and ophthalmic care when it comes to preventing or treating ocular inflammation due to trauma, chemicals, infections, allergies or other causes. Corticosteroids are synthetic drugs that mimic steroid hormones naturally produced by the body. These steroid hormones have a wide variety of actions and control functions that are involved in a number of important physiological systems including stress responses, immune responses, inflammatory responses, carbohydrate metabolism, protein catabolism and blood electrolyte levels. In addition to regulating inflammation, corticosteroids also have the ability to affect these other physiological systems, resulting in many potential risks and side effects. Corticosteroids useful in the presently disclosed compositions and methods include, but are not limited to, prednisolone, difluprednate, loteprednol etabonate, fluorometholone, dexamethasone, rimexolone, medrysone, triamcinolone acetonide, and pharmaceutically acceptable equivalents and derivatives thereof.

For topical treatment, corticosteroids, such as prednisolone have proven to be particularly useful due to their marked antiphlogistic and antiproliferative properties. Prednisolone, in particular, has an especially potent anti-inflammatory effect and a favorable safety profile. Thus, in particular embodiments, the presently disclosed compositions and methods comprise prednisolone and/or a salt or derivative thereof, such as prednisolone acetate, prednisolone pivalate, or prednisolone phosphate. In some of these embodiments, the prednisolone salt is prednisolone acetate.

In certain embodiments, the concentration (weight/volume) of corticosteroids (e.g., prednisolone, dexamethasone) in the presently disclosed compositions is between 0.05 and 2%, including, but not limited to, 0.05% (w/v), 0.06% (w/v), 0.07% (w/v), 0.08% (w/v), 0.09% (w/v), 0.1% (w/v), 0.2% (w/v), 0.3% (w/v), 0.4% (w/v), 0.5% (w/v), 0.6% (w/v), 0.7% (w/v), 0.8% (w/v), 0.9% (w/v), 1% (w/v), 1.1% (w/v), 1.2% (w/v), 1.3% (w/v), 1.4% (w/v), 1.5% (w/v), 1.6% (w/v), 1.7% (w/v), 1.8% (w/v), 1.9% (w/v), and 2% (w/v). In some of these embodiments, the presently disclosed compositions comprise corticosteroids (e.g., prednisolone) at a concentration between 0.25% (w/v) and 1% (w/v). In particular embodiments, the concentration of the corticosteroid (e.g., prednisolone) within the presently disclosed compositions is about 0.5% (w/v).

In another embodiment, the corticosteroids is included in an amount of about 0.05% (w/v) to about 1.75% (w/v), or from 0.10% (w/v) to 1.50% (w/v), or 0.15% (w/v) to 1.25% (w/v), or 0.20% (w/v) to 0.100% (w/v), or 0.25% (w/v) to 0.75% (w/v), or 0.30% (w/v) to 0.50% (w/v), or 0.35% (w/v) to 0.45% (w/v), or from 0.40% (w/v) to 0.45% (w/v).

In a further embodiment, the corticosteroids is included in an amount of about 0.05% (w/v) ±0.05 (w/v), 0.10% (w/v) ±0.05 (w/v), 0.20% (w/v) ±0.10 (w/v), 0.30% (w/v) ±0.25 (w/v), 0.40% (w/v) ±0.25 (w/v), or about 0.50% (w/v) ±0.25 (w/v), or about 0.60% (w/v) ±0.50 (w/v), or about 0.70% (w/v) ±0.50 (w/v), or about 0.80% (w/v) ±0.75 (w/v), or about 0.90% (w/v) ±0.75 (w/v), or about 1.0% (w/v) ±1.0 (w/v), or about 1.1% (w/v) ±1.0 (w/v), or about 1.2% (w/v) ±1.0 (w/v), or about 1.3% (w/v) ±1.25 (w/v), or about 1.4% (w/v) ±1.25 (w/v), or about 1.50% (w/v) ±1.50 (w/v), or about 1.6% (w/v) ±1.5 (w/v), or about 1.7% (w/v) ±1.5 (w/v), or about 1.8% (w/v) ±1.75 (w/v), or from about 1.9% (w/v) ±1.75 (w/v).

In an alternative embodiment, the corticosteroids is included in an amount of about 0.05% (w/v) to about 0.10% (w/v), or from 0.10% (w/v) to 0.20% (w/v), or 0.20% (w/v) to 0.30% (w/v), or 0.30% (w/v) to 0.40% (w/v), or 0.40% (w/v) to 0.50% (w/v), or 0.50% (w/v) to 0.60% (w/v), or 0.60% (w/v) to 0.70% (w/v), or 0.70% (w/v) to 0.80% (w/v), or 0.80% (w/v) to 0.90% (w/v), or 0.90% (w/v) to 1.0% (w/v), or 1.1% (w/v) to 1.2% (w/v), or 1.2% (w/v) to 1.3% (w/v), or 1.3% (w/v) to 1.4% (w/v), or 1.4% (w/v) to 1.5% (w/v), or 1.5% (w/v) to 1.6% (w/v), or 1.6% (w/v) to 1.7% (w/v), or 1.7% (w/v) to 1.8% (w/v), or 1.8% (w/v) to 1.9% (w/v), or 1.9% (w/v) to 2.0% (w/v). In another embodiment, the corticosteroids is included in an amount of about 0.05% (w/v) to about 0.15% (w/v), or from 0.15% (w/v) to 0.25% (w/v), or 0.25% (w/v) to 0.35% (w/v), or 0.35% (w/v) to 0.45%, 0.45% (w/v) to 0.55% (w/v), or 0.55% (w/v) to 0.65% (w/v), or 0.65% (w/v) to 0.75% (w/v), or 0.75% (w/v) to 0.85% (w/v), or 0.85% (w/v) to 0.95% (w/v), or 0.95% (w/v) to 1.05% (w/v), or 1.05% (w/v) to 1.15% (w/v), or 1.15% (w/v) to 1.25% (w/v), or 1.25% (w/v) to 1.35% (w/v), or 1.35% (w/v) to 1.45% (w/v), or 1.45% (w/v) to 1.55% (w/v), or 1.55% (w/v) to 1.65% (w/v), or 1.65% (w/v) to 1.75% (w/v), or 1.75% (w/v) to 1.85% (w/v), or from 1.85% (w/v) to 1.95% (w/v).

A second class of anti-inflammatory drugs, namely non-steroidal anti-inflammatory drugs (NSAIDs) such as diclofenac, can also be found in the presently disclosed compositions and methods. An additional benefit of NSAIDs, besides their anti-inflammatory action, is their analgesic properties. Moreover, NSAIDs inhibit miosis (pupil constriction) which is useful in the setting of ocular surgery. Thirdly, NSAIDs are used after ocular surgery for the prevention and treatment of cystoid macular edema (CME, retinal swelling), a common and known side effect after cataract surgery that affects 4-21% of patients. Non-limiting examples of NSAIDs useful in the presently disclosed compositions and methods include ketorolac tromethamine, bromfenac, diclofenac, nepafenac, pharmaceutically acceptable equivalents and derivatives thereof. In particular embodiments, the presently disclosed compositions and methods comprise diclofenac.

In certain embodiments, the concentration (weight/volume) of NSAIDs (e.g., diclofenac, bromfenac) in the presently disclosed compositions is between 0.05% and 0.5% (w/v) (weight/volume), including, but not limited to, 0.05% (w/v), 0.06% (w/v), 0.07% (w/v), 0.08% (w/v), 0.09% (w/v), 0.1% (w/v), 0.11% (w/v), 0.12% (w/v), 0.13% (w/v), 0.14% (w/v), 0.15% (w/v), 0.16% (w/v), 0.17% (w/v), 0.18% (w/v), 0.19% (w/v), 0.2% (w/v), 0.21% (w/v), 0.22% (w/v), 0.23% (w/v), 0.24% (w/v), 0.25% (w/v), 0.26% (w/v), 0.27% (w/v), 0.28% (w/v), 0.29% (w/v), 0.3% (w/v), 0.31% (w/v), 0.32% (w/v), 0.33% (w/v), 0.34% (w/v), 0.35% (w/v), 0.36% (w/v), 0.37% (w/v), 0.38% (w/v), 0.39% (w/v), 0.4% (w/v), 0.41% (w/v), 0.42% (w/v), 0.43% (w/v), 0.44% (w/v), 0.45% (w/v), 0.46% (w/v), 0.47% (w/v), 0.48% (w/v), 0.49% (w/v), and 0.5% (w/v). In some of these embodiments, the presently disclosed compositions comprise NSAIDs (e.g., diclofenac) at a concentration between 0.05% and 0.2% (w/v). In particular embodiments, the concentration of the NSAID (e.g., diclofenac) within the presently disclosed compositions is about 0.1% (w/v).

In another embodiment, the NSAID is included in an amount of about 0.05% (w/v) to about 0.50% (w/v), or from 0.10% (w/v) to 0.45% (w/v), or 0.15% (w/v) to 0.40% (w/v), or 0.20% (w/v) to 0.35% (w/v), or from 0.25% (w/v) to 0.30% (w/v).

In a further embodiment, the NSAID is included in an amount of about 0.05% (w/v) 0.05 (w/v), 0.10% (w/v) ±0.5 (w/v), 0.20% (w/v) ±0.75 (w/v), 0.30% (w/v) ±0.75 (w/v), 0.40% (w/v) ±0.75 (w/v), or from about 0.50 (w/v) ±0.25 (w/v).

In an alternative embodiment, the NSAID is included in an amount of about 0.05% (w/v) to about 0.10% (w/v), or from 0.10% (w/v) to 0.15% (w/v), or 0.15% (w/v) to 0.20% (w/v), or 0.25% (w/v) to 0.30% (w/v), or 0.30% (w/v) to 0.35% (w/v), or 0.35% (w/v) to 0.40% (w/v), or 0.40% (w/v) to 0.45% (w/v), or from 0.45% (w/v) to 0.50% (w/v). In another embodiment, the NSAID is included in an amount of about 0.05% (w/v) to about 0.15% (w/v), or from 0.15% (w/v) to 0.25% (w/v), or 0.25% (w/v) to 0.35% (w/v), or from 0.35% (w/v) to 0.45%.

Until now, no combination drugs comprising both corticosteroids and NSAIDs exist in the market. Furthermore, combining two different classes of anti-inflammatory drugs such as diclofenac and prednisolone for the treatment of eye conditions, such as post-operative inflammation provides several benefits. First, such a composition combines the potent anti-inflammatory action of a corticosteroid with those of an NSAID, resulting in an additive, synergistic anti-inflammatory, and/or unexpectedly beneficial medical effect in terms of preventing and/or treating the eye conditions and diseases discussed herein. Additionally, NSAIDs are approved for post-operative pain management of cataract surgery, the maintenance of mydriasis during surgery, and for the prevention and treatment of CME. Moreover, unlike diclofenac, which is approved for post-operative management, prednisolone, is indicated for the treatment of many kinds of ocular inflammation such as conjunctivitis, keratitis, and uveitis. Clinical data show that treatment using a combination of a corticosteroid such as prednisolone and an NSAID such as ketorolac displays superior clinical efficacy in treating and/or preventing CME than monotherapy with prednisolone or NSAID alone (Heier et al., *American Academy of Ophthalmology*, Vol. 107, No. 11, 2000).

In the case of inflammation that occurs concomitantly with a bacterial infection or the risk of bacterial infection, the presently disclosed compositions and methods comprise a combination of anti-inflammatory drugs with an appropriate antibiotic.

A typical scenario in which the combined treatment with anti-inflammatory drugs and antibiotics is indicated is ocular surgery. The surgical intervention typically induces an inflammatory response and due to the incision, the danger of infection is high.

In some embodiments, the presently disclosed compositions comprise a broad spectrum antibiotic. As used herein, the term "broad spectrum antibiotic" refers to an antibiotic that is effective against a wide range of bacterial species spanning different bacterial families. In some embodiments, the broad spectrum antibiotic is effective against species that are either Gram-negative or Gram-positive bacteria.

In some embodiments, the antibiotic is a gyrase inhibitor, such as ofloxacin. The presently disclosed compositions and methods can comprise an antibiotic within the class of quinolones, such as fluoroquinolones. Quinolones are broad-spectrum antibiotics that prevent bacterial DNA from unwinding and duplicating and have the following core structure, wherein the fluorine (F) substituent may or may not be present (Formula I):

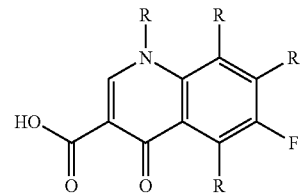

Formula I

In some embodiments, the antibiotic is a fluoroquinolone, which is a quinolone antibiotic having a fluorine atom attached to the central ring system. Such an antibiotic is effective against both Gram-negative and Gram-positive bacteria. One example is ciprofloxacin, one of the most widely used antibiotics worldwide.

Non-limiting examples of antibiotics useful in the presently disclosed compositions and methods include, but are not limited to, gatifloxacin, moxifloxacin, ciprofloxacin, ofloxacin, levofloxacin, besifloxacin, fluoroquinolone, pharmaceutically acceptable equivalents and derivatives thereof. Other antibiotics may include, but are not limited to, penicillins, aminoglycosides, macrolides, monobactams, rifamycins, tetracyclines, chloramphenicol, clindamycin, lincomycin, imipenem, fusidic acid, novobiocin, fosfomycin, fusidate sodium, neomycin, polymyxin, capreomycin, colistimethate, colistin, gramicidin, minocycline, doxycycline, vanomycin, bacitracin, kanamycin, gentamycin, erythromycin, and cephalosporins. In certain embodiments, the compositions and methods comprise ofloxacin because of its wide spectrum of action and its ability to efficiently penetrate tissues.

In certain embodiments, the concentration (weight/volume) of antibiotics (e.g., ofloxacin) in the presently disclosed compositions is between 0.1% (w/v) and 1% (w/v), including, but not limited to, 0.1% (w/v), 0.2% (w/v), 0.3% (w/v), 0.4% (w/v), 0.5% (w/v), 0.6% (w/v), 0.7% (w/v), 0.8% (w/v), 0.9% (w/v), and 1% (w/v). In some of these embodiments, the presently disclosed compositions comprise antibiotics (e.g., ofloxacin) at a concentration between 0.2% (w/v) and 0.5% (w/v). In particular embodiments, the concentration of the antibiotic (e.g., ofloxacin) within the presently disclosed compositions is about 0.3% (w/v).

In another embodiment, the antibiotic is included in an amount of about 0.10% (w/v) to about 0.90% (w/v), or from 0.20% (w/v) to 0.80% (w/v), or 0.30% (w/v) to 0.70% (w/v), or 0.40% (w/v) to 0.60% (w/v), or from 0.45% (w/v) to 0.55% (w/v).

In a further embodiment, the antibiotic is included in an amount of about 0.10% (w/v) ±0.05 (w/v), 0.20% (w/v) ±0.10 (w/v), 0.30% (w/v) ±0.25 (w/v), 0.40% (w/v) ±0.25 (w/v), 0.50% (w/v) ±0.45 (w/v), or about 0.60 (w/v) ±0.50 (w/v), or about 0.70 (w/v) ±0.50 (w/v), or about 0.80 (w/v) ±0.75 (w/v), or about 0.90 (w/v) ±0.75 (w/v), or from about 0.90 (w/v) ±0.75 (w/v).

In an alternative embodiment, the antibiotic is included in an amount of about 0.10% (w/v) to about 0.15% (w/v), or from 0.15% (w/v) to 0.20% (w/v), or 0.20% (w/v) to 0.25% (w/v), or 0.25% (w/v) to 0.30% (w/v), or 0.30% (w/v) to 0.35% (w/v), or 0.35% (w/v) to 0.40% (w/v), or 0.40% (w/v) to 0.45% (w/v), or 0.45% (w/v) to 0.50% (w/v), or 0.50% (w/v) to 0.55% (w/v), or 0.55% (w/v) to 0.60% (w/v), or 0.60% (w/v) to 0.65% (w/v), or 0.65% (w/v) to 0.70% (w/v), or 0.70% (w/v) to 0.75% (w/v), or 0.75% (w/v) to 0.80% (w/v), or 0.80% (w/v) to 0.85% (w/v), or 0.85% (w/v) to 0.90% (w/v), or 0.90% (w/v) to 0.95% (w/v), or from 0.95% (w/v) to 1.0% (w/v). In another embodiment, the antibiotic is included in an amount of about 0.10% (w/v) to about 0.20% (w/v), or from 0.20% (w/v) to 0.30% (w/v), or 0.30% (w/v) to 0.40% (w/v), or 0.40% (w/v) to 0.50% (w/v), or 0.50% (w/v) to 0.60% (w/v), or 0.60% (w/v) to 0.70% (w/v), or 0.70% (w/v) to 0.80% (w/v), or 0.80% (w/v) to 0.90% (w/v), or from 0.90% (w/v) to 1.00% (w/v).

Likewise, until now, no combination drugs comprising both an antibiotic and an NSAID, or drugs comprising all three agents (e.g., an antibiotic, an NSAID, and a corticosteroid) exist in the market. Such a combination composition provides the potent antibiotic action of a broad spectrum antibiotic with the aid of an NSAID, resulting in an additive, synergistic antibiotic, and/or unexpectedly beneficial medical effect in terms of preventing and/or treating the eye conditions and diseases discussed herein. For instance, in one reported study, CME patients were enrolled in a study to examine the benefits of daily ocular dropwise addition of an antibiotic and an NSAID. In this study, the postoperative regimen of CME patients included administration of both TobraDex® (tobramycin-dexamethasone, an antibiotic) and Acular® (ketorolac tromethamine, an NSAID) drops, 4 times per day, to a total of 5 cc and 10 cc, respectively, in each eye. Remarkably, this study found no cases of postoperative CME or iritis in 540 consecutive eyes after this treatment regimen (Arshinoff et al, *J Cataract Refract Surg*, Vol. 29, July 2003). These drops were administered separately and not as one formulation. Had this medication been delivered as a simple, easy-to-use, efficient, and synergistic formulation comprising the NSAID, the corticosteroid, and the antibiotic in one application, even more profound outcomes likely would have been observed. Thus, in some embodiments, the compositions described herein include an NSAID (e.g., diclofenac) and an antibiotic (e.g., ofloxacin). In yet another embodiment, the composition includes a corticosteroid (e.g., prednisolone) and an antibiotic (e.g., ofloxacin). In certain embodiments, the composition comprises a corticosteroid (e.g., prednisolone) and an NSAID (e.g., diclofenac). In certain embodiments, the composition comprises a corticosteroid (e.g., prednisolone), an NSAID (e.g., diclofenac), and an antibiotic (e.g., ofloxacin).

The ophthalmic composition disclosed herein, in one embodiment, are used for the prevention and/or treatment of eye conditions. Thus, pharmaceutical compositions for the treatment or prevention of eye diseases or conditions in a subject are also provided herein comprising the presently disclosed compositions and a pharmaceutically acceptable carrier.

In some embodiments, the presently disclosed compositions comprise a complexing agent. In an embodiment, the complexing agent has a hydrophobic core and a hydrophilic exterior. An example of a complexing agent is β-cyclodextrin, which may be 2-Hydroxypropyl-gamma-cyclodextrin, methyl-β-cyclodextrin, hydroxypropyl-β-cyclodextrin, or any derivative thereof. Cyclodextrins are relatively large cyclic carbohydrates that are conical in shape. This structure can form supramolecular inclusion host-guest particles, wherein cyclodextrin is the host molecule and the active ingredient is the guest molecule residing within the hydrophobic core of cyclodextrin. The host-guest complex is be generated by physically mixing the complexing agent (e.g., cyclodextrin molecule) with the active ingredient.

Those skilled in the art will appreciate that both natural and chemically modified cyclodextrins are readily available in the art and may be used in the present invention to increase the biological activity of an active ingredient (see "Comprehensive Supramolecular Chemistry" Volume 3, edited by József Szejtili and Tetsuo Osa, published by Elsevier Science Inc., New York, N.Y.). Naturally occurring cyclodextrins include α-, β-, and γ-cyclodextrins (Pagington, Chemistry in Britain, 23:455 (1987); Parrish, Cyclodextins-A Review, Stering Organics Ltd. Newcastel-Upon-Tyne. England; Szejtli, Cyclodextrin Technology: Topics in Inclusion Science, Kluwer Academic Publishers (1988)). Modifications of natural cyclodextrins can also easily be made and include, for example, glucosyl-α-cyclodextrin, maltosyl-α-cyclodextrin, glucosyl-β-cyclodextrin, and maltosyl-β-cyclodextrin.

Those skilled in the art will further appreciate that many different chemical moieties may be introduced into the cyclodextrin molecule and such chemically modified cyclodextrins are readily available (see, e.g., Yoahida et al., *Int. Pharm.*, 46:217 (1988); Muller et al., *J. Pharm. Sci.*, 75(6): June 1986; Irie et al., *Pharm. Res.*, No. 11, p. 713 (1988)). In one example, chemically modified cyclodextrins are generated by reaction of the hydroxyl groups lining the upper and lower ridges of the toroid of cyclodextrin with, for example, methyl, hydroxyethyl, hydoxylpropyl, carboxymethyl, or acetyl. Each cyclodextrin hydroxyl group differs in its chemical reactivity so that the reaction process produces an amorphous mixture of thousands of positional and optical isomers. The hydroxypropyl-β-cyclodextrin system is a highly complex mixture of various isometric forms of variously substituted β-cyclodextrin derivatives. This property of amorphousness is important to certain physiochemical properties of the chemically modified cyclodextrins and has beneficial effects on aqueous solubility and toxicity of the crystalline parent molecule (Yoshida et al., supra; Muller et al., supra; Irie et al., supra; Muller et al., *Pharm Res.*, 10:309 (1985)).

Those skilled in the art will appreciate that complexing agents such as cyclodextrin may be used to optimize the bioactivity or efficacy of an active ingredient. Furthermore, complexing agents can be used to stabilize the NSAID and the antibiotic by building a complex. Without the complexing agent, such as cyclodextrin, the NSAID or antibiotic will oxidize. Formulations may be further optimized by derivatization of a cyclodextrin molecule to optimize the concentration, storage, manufacturing requirements, or route of administration of the active ingredient.

Typical ophthalmologically acceptable carriers for the compositions disclosed herein include, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate, and other conventionally employed acceptable carriers. In some embodiments, the pharmaceutical composition also contains non-toxic auxiliary substances such as emulsifying, preserving, wetting agents, bodying agents and the like, such as for example, polyethylene glycols 200, 300, 400, and 600, carbowaxes 1,000, 1,500, 4,000, 6,000, and 10,000, antibacterial components such as quaternary ammonium compounds, phenylmercuric salts known to have cold sterilizing properties and which are non-injurious in use, thimerosal, benzalkonium chloride, methyl and propyl paraben, benzyldodecinium bromide, benzyl alcohol, phenylethanol, buffering ingredients such as sodium chloride, sodium borate, sodium acetate, or gluconate buffers, and other conventional ingredients such as dextrose, maltodextrin, glycerol, ethanol, sorbitan monolaurate, triethanolamine, polyoxyethylene sorbitan monopalmitylate, dioctyl sodium sulfosuccinate, monothioglycerol, thiosorbitol, ethylenediamine tetra-acetic acid, and the like. Additionally, suitable ophthalmic vehicles are used as carrier media in some embodiments for the present purpose including conventional phosphate buffer vehicle systems, isotonic boric acid vehicles, isotonic sodium chloride vehicles, isotonic sodium borate vehicles and the like. Optionally, in some embodiments, the compositions further comprise other additives such as, for example, inert gases (e.g., nitrogen, helium, neon, argon, krypton, xenon).

The pharmaceutical composition is formulated in a number of different ways according to the present disclosure. Ophthalmic formulations include but are not limited to ocular injections such as intravitreal, subtenons, subconjunctival, periocular, retrobulbar injections; topical ophthalmic aqueous solutions, such as suspensions, ointments, and gels; intraocular biodegradable and non-biodegradable implants; implants that are inserted through incisions made in the eye wall or sutured around the globe of the eye; tack for intraocular drug delivery; and bioadhesive ophthalmic inserts.

In some topical embodiments involving ophthalmic administration, the presently disclosed compositions take the form of solutions, gels, ointments, suspensions, or solid inserts, formulated so that a unit dosage comprises an effective amount of each active component (i.e., at least two of corticosteroid, NSAID, and antibiotic) or some submultiple thereof.

In cataract surgery, the most prevalent side effect (more than 80% of patients) is ocular discomfort due to dry eyes. Thus, artificial tear products are often given to patients to relieve ocular discomfort. The majority of commercial artificial tears contain viscoelastic polymers such as hypromellose (hydroxypropylmethylcellulose), carbomer, or hyaluronic acid as viscosifying agents. In some embodiments the presently disclosed compositions include one or more viscosifying agents to reduce post-operative ocular discomfort. In some embodiments, the viscosifying agent is a viscoelastic polymer. Non-limiting examples of viscoelastic polymers useful in the presently disclosed compositions and methods include, but are not limited to, polymeric cellulose, polysaccharides, polyacrylic acid, polymeric alcohol such as polyvinylalcohol, hyaluronic acid, derivatives, and salts thereof.

In some embodiments, the composition is a topical eye gel. A viscosifying agent is needed to create a gel formulation. However, many viscosifying agents are ionogenic (e.g. polyacrylic acid, which is a carbomer) and thus incompatible with certain NSAIDs, such as diclofenac. Moreover, some viscosifying agents (e.g. kollidon) are unsuitable to reach a viscosity required to make a stable suspension for this purpose. As a result, no ophthalmic formulations containing diclofenac exist on the market as gel formulations. As disclosed herein, methylcellulose is an effective viscosifying agent for compositions comprising diclofenac. Thus, in some embodiments, the viscosifying agent within the presently disclosed compositions is methylcellulose (MC).

The concentration of the viscosifying agent is critical. Prednisolone acetate is micronized and very poorly water soluble and is therefore present in particulate form and sediments in liquid solutions within less than one minute. Thus, the viscosity of the composition must be high enough to form a stable gel that does not allow sedimentation of prednisolone acetate. Further, the viscosity must be high enough to cause a significant clinical effect, meaning the retention of the eye gel on the eye should be good enough in order to be efficacious and to reduce the dosage of at least one of the active ingredients. On the other side, the viscosity must not be too high so as to remain droppable. Further, a too high viscosity generally can lead to ocular discomfort (stickiness, impairment of vision similar to eye ointments), which should be avoided.

In some embodiments, the concentration of the viscosifying agent (e.g., methylcellulose) is between about 1% and about 5% (weight/volume) of the total volume of the presently disclosed compositions, including, but not limited to, 1% (w/v), 1.5% (w/v), 2% (w/v), 2.5% (w/v), 3% (w/v), 3.5% (w/v), 4% (w/v), 4.5% (w/v), and 5% (w/v). In particular embodiments, the presently disclosed compositions comprise between about 2% and about 4% of a viscosifying agent (e.g., methylcellulose).

In another embodiment, the viscosifying agent is included in an amount of about 1.0% (w/v) to about 4.50% (w/v), or from 1.50% (w/v) to 4.0% (w/v), or 2.0% (w/v) to 3.50% (w/v), or from 2.5% (w/v) to 3.0% (w/v).

In a further embodiment, the viscosifying agent is included in an amount of about 1.0% (w/v) ±0.50 (w/v), 1.5% (w/v) ±1.0 (w/v), 2.0% (w/v) ±1.5 (w/v), 2.5% (w/v) ±2.0 (w/v), 3.0% (w/v) ±2.5 (w/v), or about 3.5% (w/v) ±3.0 (w/v), or about 4.0% (w/v) ±3.50 (w/v), or about 4.5% (w/v) ±4.0 (w/v).

In an alternative embodiment, the viscosifying agent is included in an amount of about 1.0% (w/v) to about 1.50% (w/v), or from 1.5% (w/v) to 2.0% (w/v), or 2.0% (w/v) to 2.5% (w/v), or 2.5% (w/v) to 3.0% (w/v), or 3.0% (w/v) to 3.50% (w/v), or 3.50% (w/v) to 4.0% (w/v), or 4.0% (w/v) to 4.5% (w/v), or from 4.5% (w/v) to 5.0% (w/v). In another embodiment, the viscosifying agent is included in an amount of about 0.75% (w/v) to about 1.25% (w/v), or from 1.25% (w/v) to 1.75% (w/v), or 1.75% (w/v) to 2.25% (w/v), or 2.25% (w/v) to 2.75%, 2.75% (w/v) to 3.25% (w/v), or 3.25% (w/v) to 3.75% (w/v), or 3.75% (w/v) to 4.25% (w/v), or 4.25% (w/v) to 4.75% (w/v), or from 4.75% (w/v) to 5.25% (w/v).

The presently disclosed pharmaceutical compositions also include, in some embodiments, a gum such as gellan gum, for example, at a concentration of about 0.1 to about 2% by weight.

After surgery, eyes are sensitive to synthetic chemicals, therefore in some embodiments, the presently disclosed compositions are substantially preservative-free. As used herein, the term "preservative" refers to a compound that when added to a composition prevents the degradation of components of the composition through microbial growth or action or undesired chemical changes. In some of those embodiments wherein the composition is substantially preservative-free, inert gases may still be present.

The presently disclosed compositions can comprise multiple doses (i.e., a multi-dose container) considering many patients with eye conditions are advanced in age, making small single dose units difficult to handle.

III. Methods of Using the Ophthalmic Compositions

Methods of treating or preventing ophthalmic conditions in a subject comprise administering to a subject in need thereof an effective amount of the presently disclosed ophthalmic compositions.

The presently disclosed compositions, described above, are intended to be administered topically by direct or indirect application to the eye. In various embodiments, as described above, the compositions are in the form of a gel, a liquid, a suspension, a solution, an ointment, a mist, or an aerosol.

In one embodiment, treatment includes the application or administration of an ophthalmic composition as described herein to a subject, where the subject has, or is at risk of developing an ophthalmic condition. In another embodiment, treatment includes the application or administration of an ophthalmic composition comprising an NSAID and a corticosteroid to a subject where the subject is at risk of developing CME. In another embodiment, the treatment includes application or administration of an ophthalmic composition comprising an NSAID and an antibiotic. In another embodiment, the treatment includes application or administration of an ophthalmic composition comprising a corticosteroid and an antibiotic. In a further embodiment, the composition comprises all three API, including an NSAID, a corticosteroid, and an antibiotic. It should be appreciated by one skilled in the art that treating a patient with a single composition comprising a combination of an NSAID and a corticosteroid, or a combination of an NSAID and an antibiotic, or a combination of a corticosteroid and an antibiotic, or a combination of all three active agents (e.g., NSAID, corticosteroid, and an antibiotic) has benefits over treating patients with each therapy separately as it will increase patient adherence to the treatment protocol leading potentially to a reduction in the length of time needed to administer the drops, and a concomitant reduction in medical cost.

In accordance with the present invention, the ophthalmic composition as described herein can be used to promote a positive therapeutic response with respect to the ophthalmic condition. A "positive therapeutic response" with respect to the ophthalmic condition is intended to include an improvement in the disease that can be evidenced by, for example, a delayed onset of clinical symptoms of the condition, a reduction in severity of some or all clinical symptoms of the condition, a slower progression of the condition, an improvement in the overall health or well-being of the subject, or by other parameters well known in the art that are specific to the particular condition.

In keeping with the scope of the present disclosure, the ophthalmic composition as described herein are administered to a human or other animal in accordance with the aforementioned methods of treatment in an amount sufficient to produce a therapeutic effect. In an embodiment, the ophthalmic composition is administered to such a human or other animal in a conventional dosage form prepared by combining the ophthalmic composition described herein with a conventional pharmaceutically acceptable carrier according to known techniques. In accordance with one embodiment, the ophthalmic composition is administered to such a human or animal concurrently with another medication such as, but not limited to, subconjunctival injection of triamcinolone acetonide and/or an intravitreal injection of bevacizumab. It will be recognized by one of skill in the art that the form and character of the pharmaceutically acceptable carrier is dictated by the amount of active ingredient with which it is to be combined, the route of administration and other well-known variables.

In another embodiment, the ophthalmic composition as described herein is useful in the prevention of various ophthalmic conditions. The term "prevention" is well known in the art and is defined hereinabove. For example, a subject suspected of being prone to suffer from a condition as defined herein may, in particular, benefit from a prevention of the condition. The subject may have a susceptibility or predisposition for the condition, including but not limited to hereditary predisposition. Such a predisposition can be determined by standard assays, using, for example, genetic markers or phenotypic indicators. In one embodiment, a condition to be prevented has not yet been diagnosed or cannot be diagnosed in the subject (for example, the subject does not show any clinical or pathological symptoms). Thus, the term "prevention" therefore includes the use of the presently disclosed compositions before any clinical and/or pathological symptoms are diagnosed or determined or can be diagnosed or determined by an attending physician. Prevention includes, without limitation, to avoid the condition from occurring in the subject that may be predisposed to the disease but does not yet experience or exhibit symptoms of the disease (prophylactic or preventative care).

Patients with an increased risk of developing CME and/or ocular inflammation include but are not limited to those characterized by at least one of the following characteristics:
  prolonged surgery;
  previous surgery;
  young patients (younger than 50 years);
  history of CME;
  history of diabetes mellitus
  history of uveitis;
  history of intraocular inflammation;
  existing additional ocular diseases;
  diabetic retinopathy; and
  retinal venocclusion.

The amount of ophthalmic preparation to be combined with the carrier materials to produce a single dosage form will vary depending upon the host treated and the particular mode of administration. The composition is in one embodiment administered as a single dose. In other embodiments, the compositions described herein are administered as multiple doses. Dosage regimens also can be adjusted to provide the optimum desired response (e.g., a therapeutic or prophylactic response). In one embodiment, the compositions described herein are administered at specific fixed or variable intervals, e.g., once a day, or on an "as needed" basis.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Generally, the regimen as a regular administration of the pharmaceutical composition comprising the herein defined should be, e.g., in a range as described below. Progress can be monitored by periodic assessment.

In one embodiment, the presently disclosed pharmaceutical compositions are liquid in form and administered as 1 drop into the eye as a single dose. In other embodiments, the presently disclosed compositions are administered as 2 drops, 3 drops, 4 drops, 5 drops, 6 drops, 7 drops, 8 drops, 9 drops, 10 drops, or more into the eye as a single dose. About twenty drops are equal to 1 mL of fluid.

In some embodiments, each dose of the pharmaceutical composition is administered 1, 2, 3, 4, 5, 6, 7, 8, 9, 10, 11, 12, 13, 14, 15, 16, 17, 18, 19, or 20 times per day. In some embodiments, the pharmaceutical composition is administered more than 20 times per day. In other embodiments, the presently disclosed compositions are administered at a dose of one drop between 1 and 6 times per day. In some embodiments, the composition is administered at a dose of one drop between 1 and 3 times per day.

The presently disclosed compositions are used in some embodiments to prevent or treat ophthalmic conditions that result from ocular surgery, such as cataract surgery. In these embodiments, the compositions are administered pre-operatively, peri-operatively, and/or post-operatively. In some of these embodiments, the ophthalmic composition is administered at a dose of one drop between 1 and 3 times pre-operatively. In some of those embodiments wherein the composition is administered post-operatively, the dose is one drop between 1 and 6 times per day. In particular embodiments, the dose is one drop between 1 and 3 times per day, administered post-operatively. In particular embodiments, the presently disclosed compositions are administered within the same day of the surgical procedure post-operatively and in some of these embodiments, daily for up to 4-6 weeks following the surgery.

The composition is in some embodiments administered for short periods of time or regularly for longer periods of time. In an embodiment, the composition is administered regularly for 1, 2, 3, 4, 5, 6, 7, 8, 9, 10, or more days. In other embodiments, the composition is administered regularly for 1, 2, 3, 4, 5, 6, 7, 8, 9, 10, or more weeks. In another embodiment, the composition is administered regularly for 1, 2, 3, 4, 5, 6, 7, 8, 9, 10, 11, 12, or more months. In an embodiment, the composition is administered regularly for 1, 2, 3, 4, 5, 6, 7, 8, 9, 10, or more years. As used herein, the term "regularly" refers to administration of the composition at regular or evenly spaced times or intervals over a period of time. For instance, the composition is in one embodiment administered to a patient once daily for three years. In other embodiments, the composition is administered to a patient once every other day for 5 years. It should be appreciated that the frequency of administration is varied based on a number of factors, including, but not limited to, the severity of disease, the overall health of the patient, any additional medications the patient is taking, and whether the treatment is prophylactic or not. It should also be appreciated that the frequency of administration is adjustable at any point in the treatment regimen.

In one embodiment, the composition comprising the ophthalmic preparation as described herein is used in combination with any known conventional therapy or prophylactic therapy for any of the eye conditions disclosed herein. Such conventional therapies and prophylactics are well known in the art and the skilled person knows any such therapies.

Provided are also embodiments in which the ophthalmic composition is used in the manufacture of a medicament for treating or preventing an ophthalmic condition in a subject in need thereof, wherein the medicament is used in a subject that has been pretreated or is concurrently being treated with at least one other therapy. By "pretreated" or "pretreatment" is intended the subject has received one or more other therapies prior to receiving the medicament comprising the ophthalmic composition. "Pretreated" or "pretreatment" includes subjects that have been treated with at least one other therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the ophthalmic composition. By "concurrent" or "concomitant" is intended the subject is receiving one or more other therapies while at the same time receiving the medicament comprising the ophthalmic composition. It is not necessary that the subject was a responder to pretreatment with the prior therapy or therapies or a responder to the concurrent therapy or therapies. Thus, the subject that receives the medicament comprising the ophthalmic composition could have responded, or could have failed to respond, to pretreatment with the prior therapy, or to one or more of the prior therapies where pretreatment comprised multiple therapies.

IV. Methods of Preparing Ophthalmic Compositions

Also disclosed herein are methods for preparing the presently disclosed compositions comprising at least two of a corticosteroid, an NSAID, and an antibiotic. In those embodiments wherein the composition comprises an NSAID and an antibiotic, the preparation methods comprise separately complexing the NSAID and the antibiotic with cyclodextrin. Cyclodextrin and/or other complexing agents can be used to stabilize the NSAID and the antibiotic by building a complex. Without the complexing agent, such as cyclodextrin, the NSAID or antibiotic will oxidize. In one embodiment, the methods comprise preparing the composition in the form of a gel.

In an embodiment, the composition contains the following ingredients shown in Table 1 below:

| Material | Strength (%/weight) | Function | Concentration range (w/v) |
|---|---|---|---|
| Prednisolone acetate | 0.5% | Active pharmaceutical ingredient (API) | 0.1-1.0% |
| Diclofenac-Na* | 0.01-0.1% | API | 0.01-0.15% |
| Ofloxacin | 0.3% | API | 0.1-0.5% |
| Methylcellulose** | Approx 2-4% | viscosifier | 1-5% |
| 2-hydroxypropyl-gamma-cyclodextrin*** | — | For complexation of diclofenac and ofloxacin | |
| Mannitol | 5% | To adjust Osmotic pressure Specification 280-314 mosmol/kg | |
| Sodium disulfite | 0.02% | Antioxidant | |
| NaOH/HCL | — | For pH adjustment Specification 5.5-8.5 | |
| Water | q.s. | solvent | |

*Due to the lower local tolerance of diclofenac, the concentration of diclofenac may need to be reduced from the commonly used 0.1% because diclofenac is present on the cornea for a longer time period with gel formulations versus eye drop formulations. The exact concentration will be determined in a non-clinical dose finding experiment. Prednisolone acetate and ofloxacin are both at their commonly used and approved concentrations.
**The exact concentration will be determined, but will likely lie within 2% and 4% methylcellulose. The viscosity has to be relatively high, otherwise the suspension (prednisolone acetate is present in particulate form) is not stable. This is required if the product is sold in single dose units or tubes.
***2-Hydroxypropyl-gamma-cyclodextrin is complexed with diclofenac and ofloxacin (two separate steps). The molar ratio of cyclodextrin to the API is between 1:1 and 1:2 (2x cyclodextrin).

Diclofenac and ofloxacin are generally incompatible because exposure to oxygen causes oxygenation of diclofenac which in turn results in degradation of ofloxacin into ofloxacin-N-oxide (See European Patent No. EP0994693B1, which is incorporated herein in its entirety). To solve this issue, ofloxacin and diclofenac are complexed in the described embodiment separately with cyclodextrin and stored under conditions that exclude oxygen and instead include inert gases, such as, for example, nitrogen, and/or argon.

In one embodiment, a method for preparing a composition comprising prednisolone, diclofenac, and ofloxacin in a gel formulation comprises the steps of:

a) producing a methylcellulose gel to form Solution 1;

b) complexing ofloxacin with 2-hydroxypropyl-gamma-cyclodextrin to form Solution 2;

c) complexing diclofenac with 2-hydroxypropyl-gamma-cyclodextrin to form Solution 3;

d) combining Solutions 2 and 3 to form Solution 4;

e) adjusting pH of Solution 4 to range of between 5.5 to 8.5;

f) adding mannitol to Solution 4 to form Solution 5;

g) combining Solutions 1 and 5 to form Solution 6; and h) adding prednisolone acetate to Solution 6.

Steps a)-c) are able to be performed in any order, and step a) is performed before, simultaneously, or after any one of steps b)-f).

In one embodiment, the molar ratio of cyclodextrin to each of the NSAID and antibiotic is between 1:1 and 1:2. In particular embodiments, the molar ratio of 2-hydroxypropyl-gamma-cyclodextrin to diclofenac or ofloxacin is between 1:1 and 1:2 (2× cyclodextrin).

In some embodiments, the method further comprises distributing the prepared composition into container(s) and overlaying the composition with an inert gas to exclude oxygen, followed by sealing of the container to entrap the inert gas therein. As used herein, and "inert gas" is one that does not chemically react with any component of the presently disclosed compositions under routine storage conditions. Non-limiting examples of inert gases that are suitable for use in the presently disclosed methods and compositions are nitrogen, helium, neon, argon, krypton, and xenon.

All of the references cited above, as well as all references cited herein, are incorporated herein by reference in their entireties.

While the described methods and compositions are illustrated and described in detail in above, such illustration and description are to be considered illustrative or exemplary and not restrictive. It will be understood that changes and modifications may be made by those of ordinary skill within the scope and spirit of the following claims. In particular, the present disclosure is intended to encompass any further embodiments including any combination of features from different individual embodiments described above and below. For instance, included in the disclosure are embodiments such as adding antibiotics to the ophthalmic composition, using other corticosteroids, and/or other NSAIDs not described herein but otherwise known in the art, and administrating these APIs together with at least one other medication for optimizing treatment efficacy (e.g., administering concurrently with subconjunctival injection of 40 mg triamcinolone acetonide).

The following illustrative non-limiting examples provide a better understanding of the disclosed compositions and methods and of their many advantages. The following examples are included to demonstrate preferred embodiments. It should be appreciated by those of skill in the art that the techniques disclosed in the examples which follow represent techniques that function well for their intended purpose, and thus are considered to constitute preferred modes for its practice, but are otherwise not limiting and substitutable by other known means of achieving the same outcomes. However, those of skill in the art should, in light of the present disclosure, appreciate that many changes can be made in the specific embodiments which are disclosed and still obtain a like or similar result without departing from the spirit and scope of the invention.

EXAMPLES

Example 1: An Ophthalmic Preparation

This example illustrates an embodiment of the presently disclosed ophthalmic preparations. This particular preparation incorporates the ingredients and concentrations thereof as shown in Table 2 below.

TABLE 2

| Material | Strength (%/weight) | Function | Concentration range |
|---|---|---|---|
| Prednisolone acetate | 0.5% | Active pharmaceutical ingredient (API) | 0.1-1.0% |
| Diclofenac-Na* | 0.01-0.1% | API | 0.01-0.15% |
| Ofloxacin | 0.3% | API | 0.1-0.5% |
| Methylcellulose** | Approx 2-4% | viscosifier | 1-5% |
| 2-Hydroxypropyl-gamma-cyclodextrin*** | — | For complexation of diclofenac and ofloxacin | |
| Mannitol | 5% | To adjust Osmotic pressure Specification 280-314 mosmol/kg | |
| Sodium disulfite | 0.02% | Antioxidant | |
| NaOH/HCL | — | For pH adjustment Specification 5.5-8.5 | |
| Water | q.s. | solvent | |

*Due to the lower local tolerance of diclofenac, the concentration of diclofenac may need to be reduced from the commonly used 0.1% because diclofenac is present on the cornea for a longer time period with gel formulations versus eye drop formulations. The exact concentration will be determined in a non-clinical dose finding experiment. Prednisolone acetate and ofloxacin are both at their commonly used and approved concentrations.
**The exact concentration will be determined, but will likely lie within 2% and 4% methylcellulose. The viscosity has to be relatively high, otherwise the suspension (prednisolone acetate is present in particulate form) is not stable. This is required if the product is sold in single dose units or tubes.
***2-Hydroxypropyl-gamma-cyclodextrin is complexed with diclofenac and ofloxacin (two separate steps). The molar ratio of cyclodextrin to the API is between 1:1 and 1:2 (2x cyclodextrin).

For a representative 500 g batch, the concentrations of various components of an exemplary embodiment of the disclosed compositions are shown in Table 3 below:

TABLE 3

| Material | g/500 g batch | Final concentration (%/weight) |
|---|---|---|
| Prednisolone acetate | 2.5 | 0.5% |
| Diclofenac-Na | 0.5 | 0.1% |
| 2-Hydroxypropyl-gamma-cyclodextrin* | 2.48 | |
| Ofloxacin | 1.5 | 0.3% |
| 2-Hydroxypropyl-gamma-cyclodextrin** | 6.55 | |
| Methylcellulose | 17.5 | 3.5% |
| Mannitol | 25 | 5% |
| Sodium disulfite | 0.1 | 0.02% |
| NaOH/HCL | | — |
| Water | 438.87 | q.s. |
| Total | 500 | |

*For diclofenac-Na complexation.
**For ofloxacin complexation.

Example 2: Anti-Inflammatory Efficacy and Intraocular Concentrations of Prednisolone Acetate-Diclofenac Eye Gel Vs. Prednisolone Acetate Eye Drops and Diclofenac Eye Drops as Single Preparations A sufficiently high number of adequate laboratory animals (e.g. rabbits or pigs, at least five animals per group) are used in this experiment such that statistical significance is achieved in any collected data. Ocular inflammation is experimentally induced in all animals by known methods. Animals are then divided into four treatment groups. Group 1 is treated with ophthalmic prednisolone-diclofenac eye gel. Group 2 is treated with the same concentration of ophthalmic prednisolone eye drops as used in Group 1. Group 3 is treated with the same concentration of ophthalmic diclofenac eye drops as used in Group 1. Group 4 is treated with the same concentration of ophthalmic diclofenac eye drops and prednisolone eye drops, administered as two separate formulations, as used in Group 1. Group 5 is mock treated (matrix only). The experiment is repeated using different concentrations of prednisolone acetate and diclofenac in eye gel formulation. After different time points, ocular inflammation in all treated animals is assessed using standard parameters, such as immigration of inflammatory cells into the eye, presence of inflammatory mediators, etc. As a second readout, intraocular fluid is drawn from laboratory animals at different time points to analyse intraocular API concentrations.

Results: the experiment is designed to show that the single preparation of the combination of prednisolone, acetate, and diclofenac is superior in its anti-inflammatory efficacy as compared to the single preparations of prednisolone, acetate, or diclofenac alone. This experiment may also show that, unexpectedly, the single preparation of the combination of prednisolone, acetate, and diclofenac shows not an additive, but synergistic effect, i.e. the level of inhibition of inflammation is higher than one of skill in the art would predict that the addition of the inhibitory effects would be for prednisolone, acetate, and diclofenac as compared with these APIs administered sequentially as separate formulations. Also, this experiment is designed to show that the intraocular concentrations of API are will be higher after administration of eye gel preparations as compared to eye drop formulations and thus, concentrations of APIs may be reduced when formulated as an eye gel in order to reach the equivalent clinical effect as eye drops.

Example 3: Local Tolerability of Prednisolone Acetate-Diclofenac-Ofloxacin Eye Gel Vs. Prednisolone Acetate, Diclofenac, Ofloxacin Eye Drops as Single Preparations on Human Corneas The effect of different preparations is tested on human corneas to ascertain ocular corneal toxicity.

Test drug 1: Ophthalmic prednisolone acetate-diclofenac-ofloxacin eye gel

Test drug 2: Ophthalmic prednisolone acetate eye drops

Test drug 3: Ophthalmic diclofenac eye drops

Test drug 4: Ophthalmic ofloxacin eye drops

Treatment group 5: Ophthalmic prednisolone acetate eye drops, ophthalmic diclofenac eye drops, and ophthalmic ofloxacin eye drops, administered as three separate preparations Test drug 5-x: Ophthalmic prednisolone acetate-diclofenac-ofloxacin eye gel with different concentrations of APIs.

Corneal toxicity is to be assessed upon administration of the various formulations using standard techniques known in the art, such as cell cultures of both presumed target cells and non-target cells for the assessment of ocular irritation. The experiment is designed to show that the eye gel formulation is tolerated better than the eye drop formulations and causes less local side effects.

Example 4: Local Tolerability of Prednisolone Acetate-Diclofenac-Ofloxacin Eye Gel Vs. Prednisolone Acetate, Diclofenac, Ofloxacin Eye Drops as Single Preparations in Healthy Volunteers A sufficiently high number of human healthy adult volunteers are to be included in this study. Group 1 is treated with ophthalmic prednisolone-diclofenac-ofloxacin eye gel. Group 2 is treated with the same concentration of ophthalmic prednisolone eye drops as used in Group 1. Group 3 is treated with the same concentration of ophthalmic diclofenac eye drops as used in Group 1. Group 4 is treated with the same concentration of ophthalmic ofloxacin eye drops as used in Group 1. Group 5 is treated with the same concentration of ophthalmic prednisolone eye drops, ophthalmic diclofenac eye drops, and ophthalmic ofloxacin eye drops as used in Group 1, in three separate preparations. Group 6 is mock treated (matrix only). Ocular discomfort upon administration is determined. Ocular adverse effects and systemic adverse events (blood sugar levels) after multiple administrations (2 weeks of daily treatments) are compared between the groups.

The experiment is designed to show that the eye gel formulation is tolerated better than the eye drop formulations and causes less systemic side effects.

Example 5: Efficacy, Ocular Tolerance, Patient Compliance and Incidence of CME after Cataract Surgery Using Perioperative Prednisolone Acetate-Diclofenac-Ofloxacin Triple Combination Vs. Standard Treatment A sufficiently high number of human patients undergoing cataract surgery regarded as at risk of developing CME are included in this study. These include but are not limited to the following: prolonged surgery, previous surgery, young patients (younger than 50 years), history of CME, history of uveitis, history of intraocular inflammation, existing additional ocular diseases, diabetic retinopathy, and retinal venocclusion.

Treatment drug 1: prednisolone acetate-diclofenac-ofloxacin eye gel triple combination Treatment drug 2: prednisolone acetate eye drops+ofloxacin eye drops+ofloxacin eye drops+artificial tears Patients are randomized to either treatment group. Treatment is given to patients standard peri- and post-surgical care after cataract surgery. Post-surgery, treatment is administered the same day as the surgical procedure and for 4-6 weeks daily. Patients are followed up daily for approximately 4-6 weeks. At defined time points, patients are examined for certain parameters such as visual acuity, macular thickness, endothelial cell density, central corneal thickness, established CME as well as subjective parameters such as eye discomfort, ocular pain and patient compliance.

The primary readouts expected from this study include incidence of CME, ocular tolerance, patient compliance, direct and indirect signs of inflammation. The secondary readouts expected from this study include patient compliance with the study drug.

This experiment is designed to show that patients treated with Treatment drug 1 will exhibit equal or lower incidence of CME and retinal swelling, equal or better inflammation suppression, better patient compliance as well as equal or better ocular tolerance including eye discomfort and pain as compared to those patients that were treated with the individual drugs.

Example 6: Efficacy in CME Prevention after Cataract Surgery Using Perioperative Prednisolone Acetate-Diclofenac Combination Vs. Diclofenac Eye Drops A sufficiently high number of human patients undergoing cataract surgery regarded as at risk of developing CME are to be included in this study. These include but are not limited to the following: prolonged surgery, previous surgery, young patients (younger than 50 years), history of CME, history of uveitis, history of intraocular inflammation, history of diabetes mellitus, existing additional ocular diseases, diabetic retinopathy, and retinal venocclusion.

Treatment drug 1: prednisolone acetate-diclofenac-eye drops double combination

Treatment drug 2: diclofenac-eye drops

Patients will be randomized to either treatment group. Treatment is given to patients in standard peri- and post-surgical care after cataract surgery. For those patients in post-surgery, treatment is to be administered the same day as the surgical procedure and for 4-6 weeks daily. Patients are followed up daily for approximately 4-6 weeks. At defined time points, patients are then examined for certain parameters such as visual acuity, macular thickness, endothelial cell density, central corneal thickness, established CME as well as subjective parameters such as eye discomfort, ocular pain and patient compliance.

Primary readouts include an estimation of the incidence of CME, as well as observations concerning direct and indirect signs of inflammation.

This experiment is designed to show that patients treated with Treatment drug 1 are expected to exhibit a lower incidence of CME and retinal swelling, and equal or better inflammation suppression, as compared to those patients which were treated with treatment drug 2.

Example 7: Efficacy in CME Prevention after Cataract Surgery Using Perioperative Dexamethasone-Bromfenac Combination Vs. Bromfenac Eye Drops A sufficiently high number of human patients undergoing cataract surgery regarded as at risk of developing CME are to be included in this study. These patients may include, but are not limited to, the following patient histories and profiles: prolonged surgery, previous surgery, young patients (younger than 50 years), history of CME, history of uveitis, history of intraocular inflammation, history of diabetes mellitus, existing additional ocular diseases, diabetic retinopathy, and retinal venocclusion.

Treatment drug 1: bromfenac-eye drops

Treatment drug 2: dexamethasone-bromfenac-eye drops double combination

Treatment drug 3: dexamethasone-bromfenac-eye drops double combination and a subconjunctival injection of 40 mg triamcinolone acetonide Treatment drug 4: dexamethasone-bromfenac-eye drops double combination and an intravitreal injection of 1.25 mg bevacizumab Treatment drug 5: dexamethasone-bromfenac-eye drops double combination and a subconjunctival injection of 40 mg triamcinolone acetonide and an intravitreal injection of 1.25 mg bevacizumab.

Patients are to be randomized to all of the treatment groups. Treatment is given to patients in standard peri- and post-surgical care after cataract surgery. For those patients in the post-surgery group, treatment is administered the same day as the surgical procedure and for several weeks daily. Patients are to return to the physician for followed up visits that include direct observations of condition daily for approximately 6-12 weeks.

Primary indicators expected from this study include incidence of CME as well as observations of direct and indirect signs of inflammation.

The experiment is designed to show that patients treated with Treatment drug 1 exhibit a higher incidence of CME and other signs of inflammation and ocular conditions as compared to those patients who were treated with treatment drugs 2, 3, 4, and 5.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims disclosed herein. Although specific terms are employed herein, they are used in a generic and descriptive sense only and not for purposes of limitation.

That which is claimed:

1. A composition comprising a non-steroidal anti-inflammatory drug (NSAID), a corticosteroid, and an antibiotic, wherein:
   the NSAID is diclofenac, or a salt thereof, and is present at between 0.05% and 0.2% (w/v) of the total volume of the composition,
   the corticosteroid is prednisolone, or a salt thereof, and is present at between 0.25% and 0.5% (w/v) of the total volume of the composition,
   the antibiotic is ofloxacin, or a salt thereof, and is present at between 0.1% and 0.2% (w/v) of the total volume of the composition, and
   the composition is formulated as an eye gel.

2. The composition of claim 1, wherein the concentration of the NSAID is between 0.05% and 0.1% (weight/volume) of the total volume of the composition.

3. The composition of claim 1, wherein the concentration of diclofenac is about 0.1% (weight/volume) of the total volume of the composition.

4. The composition of claim 1, wherein the concentration of the corticosteroid is between 0.05% and 0.1% (weight/volume) of the total amount of the composition.

5. The composition of claim 1, wherein the prednisolone salt is prednisolone acetate.

6. The composition of claim 5, wherein the concentration of prednisolone or prednisolone acetate is about 0.5% (weight/volume) of the total amount of the composition.

7. The composition of claim 1, wherein the composition further comprises a complexing agent.

8. The composition of claim 7, wherein the complexing agent is cyclodextrin, a derivative thereof, or 2-hydroxypropyl-gamma-cyclodextrin.

9. The composition of claim 1, wherein the composition further comprises a viscosifying agent.

10. The composition of claim 9, wherein the viscosifying agent is a viscoelastic polymer comprising one or more of polymeric cellulose, polysaccharides, polyacrylic acid, polymeric alcohol, hyaluronic acid, derivatives thereof, and salts thereof.

11. The composition of claim 1, wherein the composition is substantially preservative-free.

12. The composition of claim 1, wherein the composition is provided as a single dose unit.

13. The composition of claim 1, wherein prednisolone is present at about 0.5% (w/v), wherein diclofenac is present at about 0.1% (w/v), and ofloxacin is present at about 0.3% (w/v).

\* \* \* \* \*